(12) United States Patent
Matsumoto et al.

(10) Patent No.: US 6,228,653 B1
(45) Date of Patent: May 8, 2001

(54) 1,2-DIOXETANE DERIVATIVE FUSED TO PYRAN RING AND USE THEREOF

(75) Inventors: Masakatsu Matsumoto, Sagamihara; Nobuko Watanabe, Kamakura, both of (JP)

(73) Assignee: Tosoh Corporation, Yamaguchi-ken (JP)

( * ) Notice: Subject to any disclaimer, the term of this patent is extended or adjusted under 35 U.S.C. 154(b) by 0 days.

(21) Appl. No.: 09/524,003

(22) Filed: Mar. 13, 2000

(30) Foreign Application Priority Data

Mar. 12, 1999 (JP) .................................................. 11-066036

(51) Int. Cl.[7] .......................... G01N 33/00; C07D 311/00
(52) U.S. Cl. ............................ 436/93; 549/396; 548/239; 514/374; 514/456
(58) Field of Search ..................................... 574/456, 274; 548/239; 549/396; 436/93

(56) References Cited

U.S. PATENT DOCUMENTS

| 5,650,525 | 7/1997 | Matsumoto | 549/510 |
|---|---|---|---|
| 5,698,727 | 12/1997 | Matsumoto | 556/470 |
| 5,731,445 | 3/1998 | Matsumoto et al. | 549/464 |
| 5,877,333 | 3/1999 | Matsumoto et al. | 549/507 |
| 5,929,254 | 7/1999 | Matsumoto | 549/214 |
| 5,936,132 | 8/1999 | Matsumoto | 568/654 |

FOREIGN PATENT DOCUMENTS

| 0 254 051 | 1/1988 | (EP) . |
|---|---|---|
| 0 779 293 A1 | 6/1997 | (EP) . |
| WO 94/10258 | 5/1994 | (WO) . |

OTHER PUBLICATIONS

Matsumoto et al "Synthesis of 5–Alkyl–l–aryl–4, 4–dimethyl . . . " Tetrahedron Letters vol. 38 No. 16, 3.97, pp. 2863–2866.

Chan et al J. Org. Chem. (1990) 55(20), 5497–504 XP002143956 "Sensitized Photooxygenation . . . "

Le Roux et al Bull. Soc. Chim. Fr. (1971), (11), 4059–4065 XP002143957 "Thermal and photochemical..."

*Primary Examiner*—Amelia Owens
(74) *Attorney, Agent, or Firm*—Nixon & Vanderhye

(57) ABSTRACT

A 1,2-dioxetane derivative represented by the general formula:

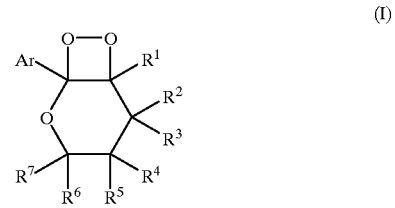

(I)

wherein $R^1$, $R^2$, $R^3$, $R^4$, $R^5$, $R^6$ and $R^7$ each independently represents hydrogen atom, an alkyl group, or an aryl group, or one or more than one pair of $R^2$ and $R^3$, $R^4$ and $R^5$, and $R^6$ and $R^7$ can together form a cyclic alkyl group. The compound is easily handled because the compound itself is very stable, and it is capable of emitting light with a very high efficiency.

10 Claims, No Drawings

1,2-DIOXETANE DERIVATIVE FUSED TO PYRAN RING AND USE THEREOF

BACKGROUND OF INVENTION

1. Field of Invention

The present invention relates to 1,2-dioxetane derivatives fused to a pyran ring and the use thereof. Since the present compounds are highly stable under an ambient conditions and emit light with a very high quantum efficiency, they can be used as chemiluminescent reagents for various assays such as immunoassay.

2. Related Art

Various 1,2-dioxetane derivatives have been synthesized, and those derivatives having at the position 3 a spiroadamantyl group are known to be useful as a substrate for chemiluminescence (see Japanese Examined Patent Publication (Kokoku) Nos. 5-21918 and 5-45590). In addition, Japanese Unexamined Patent Publication (Kokai) No. 9-216887 discloses compounds whose thermal stabilities are remarkably higher than the above-mentioned compounds, and which are useful for chemiluminescence.

However, to be useful as chemiluminescent reagents in clinical tests and the like, not only high thermal stability, but also high light-emission efficiency is required.

DISCLOSURE OF THE INVENTION

Accordingly, the present invention provides 1,2-dioxetane derivatives having not only high thermal stability but also high quantum efficiency for high emission.

More specifically, the present invention relates to a 1,2-dioxetane derivative represented by the general formula:

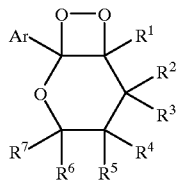

(I)

wherein $R^1$, $R^2$, $R^3$, $R^4$, $R^5$, $R^6$ and $R^7$ independently represent a hydrogen atom, an alkyl group or an aryl group; or one or more than one pair of $R^2$ and $R^3$, $R^4$ and $R^5$, and $R^6$ and $R^7$ can together form a cyclic alkyl group; and Ar represents a group represented by the formula (A):

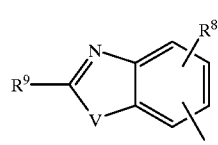

(A)

wherein $R^8$ represents a hydroxyl group, an alkoxyl group, an aralkyloxy group, a group represented by —Osi($R^{10}R^{11}R^{12}$) (wherein $R^{10}$, $R^{11}$ and $R^{12}$ independently represents an alkyl group), or a phosphate group; $R^9$ represents a hydrogen atom, an alkyl group, an aryl group, a hydroxyl group, an alkoxyl group, an aryloxy group, or an aralkyloxy group; and V represents an oxygen atom or a sulfur atom, a group represented by the formula (B):

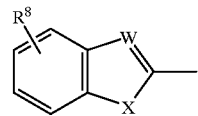

(B)

wherein $R^8$ has the same meaning as defined for $R^8$ in the above formula (A); W represents a nitrogen atom or C—$R^{13}$ (wherein $R^{13}$ represents a hydrogen atom, an alkyl group, an aryl group, an alkoxyl group, or an aralkyloxy group); and X represents an oxygen atom or a sulfur atom, or a group represented by the formula (C):

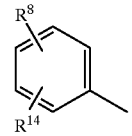

(C)

wherein $R^8$ has the same meaning as defined for $R^8$ in the above formula (A); $R^{14}$ represents a hydrogen atom, a halogen atom, an alkyl group, an alkoxyl group, or a group represented by the formula ($R^{14'}$):

($R^{14'}$)

wherein Y represents an oxygen atom, a sulfur atom, or a group represented by N—$R^{15}$; and Z represents a hydrogen atom, an alkyl group, an aryl group or a group represented by —$OR^{16}$, —$SR^{17}$ or the formula:

wherein $R^{15}$ represents a hydrogen atom, an alkyl group, an aryl group, a hydroxyl group, or an alkoxyl group; and $R^{16}$, $R^{17}$, $R^{18}$ and $R^{19}$ represent a hydrogen atom, an alkyl group or an aryl group; or one or more than one pair of $R^{15}$ and $R^{16}$, $R^{15}$ and $R^{17}$, $R^{15}$ and $R^{18}$, and $R^{18}$ and $R^{19}$ can together form a ring and this ring may contain two or more heteroatoms.

The 1,2-dioxetane derivative of the present invention is a compound capable of deriving chemiluminescence and can be used as a substrate for immunoassay.

The present invention further provides an assay reagent comprising the above-mentioned 1,2-dioxetane derivative.

The present invention further provides an assay method using the above-mentioned 1,2-dioxetane derivatives.

DETAILED DESCRIPTION OF THE INVENTION

The alkyl group for the substituents $R^1$, $R^2$, $R^3$, $R^4$, $R^5$, $R^6$ and $R^7$ is an optionally substituted straight-chain or branched alkyl group having 1 to 20 carbon atoms. The alkyl group is preferably a lower alkyl group having 1 to 6 carbon atoms, and more preferably a lower alkyl group having 1 to 4 carbon atoms. The alkyl group is exemplified by methyl, ethyl, propyl, butyl, pentyl, hexyl, heptyl, octyl, nonyl, decyl, undecyl, dodecyl, tetradecyl, pentadecyl, hexadecyl, heptadecyl, octadecyl, nonadecyl, and icosanyl. The lower alkyl group is exemplified by straight-chain or branched alkyl having 1 to 6 carbon atoms, such as methyl, ethyl, propyl, isopropyl, butyl, isobutyl, tert-butyl, a straight-chain or branched pentyl, or a straight-chain or branched hexyl.

The substituent for the alkyl group is, for example, a hydroxy group, an alkoxy group, an aryl group or a heterocyclic group. The alkoxy group is, for example, methoxy, ethoxy, propoxy, butoxy, pentyloxy, hexyloxy, methoxyethoxy, methoxypropoxy, ethoxyethoxy, ethoxypropoxy or methoxyethoxyethoxy. The aryl is, for example, a phenyl or naphthyl, and the heterocyclic group includes, for example, furyl, thienyl or pyridyl group.

The aryl group for the substituents $R^1$, $R^2$, $R^3$, $R^4$, $R^5$, $R^6$ and $R^7$ is aromatic hydrocarbon group for example, phenyl or naphthyl. The aryl may be a heteroaryl group such as furyl, thienyl, pyridyl group or the like. The aryl group can be substituted with for example, methyl, ethyl, propyl, isopropyl, butyl, isobutyl, tert-butyl, a straight-chain or branched pentyl, or a straight-chain or branched hexyl.

One or more than one pair of $R^2$ and $R^3$, $R^4$ and $R^5$, and "$R^6$ and $R^7$" together can form a cycloalkyl group having 3–8 carbon atoms. The cycloalkyl group has preferably 5–7 carbon atoms. The cycloalkyl is exemplified by cyclopropyl, cyclobutyl, cyclopentyl, cyclohexyl, cycloheptyl or the like. The cycloalkyl group may be optionally substituted by one or more substituents such as methyl, ethyl, propyl, isopropyl, butyl, isobutyl, tert-butyl, a straight-chain or branched pentyl, a straight-chain or branched hexyl, phenyl or naphthyl.

Ar in the general formula (I) can be as follows:

Formula (A):

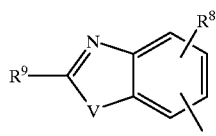

(A)

wherein $R^8$ represents a hydroxyl group, an alkoxyl group, an aralkyloxy group, a group represented by —OSi($R^{10}R^{11}R^{12}$) (wherein $R^{10}$, $R^{11}$ and $R^{12}$ independently represents an alkyl group), or a phosphate group; $R^9$ represents a hydrogen atom, an alkyl group, an aryl group, a hydroxyl group, an alkoxyl group, an aryloxy group, or an aralkyloxy group; and V represents an oxygen atom or a sulfur atom;

Formula (B):

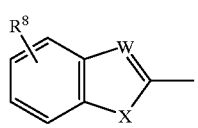

(B)

wherein $R^8$ has the same meaning as defined for $R^8$ in the above formula (A); W represents a nitrogen atom or C—$R^{13}$ (wherein $R^{13}$ represents a hydrogen atom, an alkyl group, an aryl group, an alkoxyl group, or an aralkyloxy group); and X represents an oxygen atom or a sulfur atom;

Formula (C):

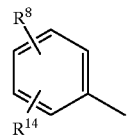

(C)

wherein $R^8$ has the same meaning as defined for $R^8$ in the above formula (A); $R^{14}$ represents a hydrogen atom, a halogen atom, an alkyl group, an alkoxyl group, or a group represented by the formula ($R^{14'}$):

($R^{14'}$)

wherein Y represents an oxygen atom, a sulfur atom, or a group represented by N—$R^{15}$; and Z represents a hydrogen atom, an alkyl group, an aryl group or a group represented by —$OR^{16}$, —$SR^{17}$ or the formula:

wherein $R^{15}$ represents a hydrogen atom, an alkyl group, an aryl group, a hydroxyl group, or an alkoxyl group; and $R^{16}$, $R^{17}$, $R^{18}$ and $R^{19}$ represent a hydrogen atom, an alkyl group or an aryl group; or one or more than one pair of $R^{15}$ and $R^{16}$, $R^{15}$ and $R^{17}$, $R^{15}$ and $R^{18}$, and $R^{18}$ and $R^{19}$ can together form a ring and this ring may contain two or more heteroatoms.

In the alkoxyl group as $R^8$, the alkyl moiety has the same meaning as defined above for alkyl group as $R^1$ to $R^7$. The alkoxy group is preferably a lower alkoxy group having 1 to 6 carbon atoms, and is exemplified by methoxy, ethoxy, n-propoxy, isopropoxy, n-butoxy, isobutoxy, tert-butoxy, straight-chain or branched pentyloxy such as n-pentyloxy, isopentyloxy, straight chain or branched hexyloxy such as n-hexyloxy, isohexyloxy, methoxyethoxy, methoxypropoxy, ethoxyethyoxy, ethoxypropoxy, methoxyethoxyethoxy, or the like.

In the aralkyloxy for $R^8$ in the formula (A), (B) and (C), the aryl moiety has the same meaning as defined above for the aryl as $R^1$ to $R^6$. The alkylene moiety in the aralkyloxy is a straight chain or branched alkylene group —$(CH_2)_n$— having 1–20 carbon atoms. The alkylene group is preferably a lower alkylene group having 1 to 4 carbon atoms, exemplified by methylene, ethylene, propylene, or butylene group. The preferred aralkyloxy is benzyloxy and phenetyloxy.

The alkyl group as $R^{10}$, $R^{11}$ and $R^{12}$ has the same meaning as defined above for $R^1$ to $R^6$. The alkyl group is preferably a lower alkyl group having 1 to 6 carbon atoms as defined above for $R^1$ to $R^6$.

The alkyl and aryl groups as $R^9$ in the formula (A) has the same meaning as defined above for $R^1$ to $R^6$. The alkyl is preferably a lower alkyl having 1 to 6 carbon atoms as defined above. The alkoxy and aralkyloxy for $R^9$ have the same meaning as defined above for $R^8$. In the aryloxy group as $R^9$, the aryl moiety has the same meaning as defined above for $R^1$ to $R^6$.

The alkyl and aryl groups as $R^{13}$ have the same meaning as defined above for $R^1$ to $R^6$. The alkoxy and aralkyloxy groups as $R^{13}$ have the same meaning as defined above for $R^8$. The alkyl is preferably a lower alkyl having 1 to 6 carbon atoms.

The alkyl group as $R^{14}$ has the same meaning as defined above for $R^1$ to $R^6$, and the alkoxy group as $R^{14}$ has the same meaning as defined above for $R^8$.

The alkyl and aryl group as Z have the same meaning as defined above for $R^1$ to $R^6$.

The alkyl and aryl groups as $R^{15}$ have the same meaning as defined above for $R^1$ to $R^6$. The alkoxy group as $R^{15}$ has the same meaning as defined above for $R^8$. The alkoxy and aryl groups for $R^{16}$, $R^{17}$, $R^{18}$ and $R^{19}$ have the same meaning as defined above for $R^1$ to $R^6$. One or more than one pair of $R^{15}$ and $R^{16}$, $R^{15}$ and $R^{17}$, or $R^{15}$ and $R^{18}$, together form a ring structure containing the nitrogen atom to which the $R^{15}$ bonds. The ring structure may contain one or more additional heteroatoms, such as nitrogen, oxygen or sulfur. The ring structure formed by $R^{18}$ and $R^{19}$ together with the nitrogen atom to which the $R^{18}$ and $R^{19}$ bind may contain one or more additional heteroatom such as nitrogen, oxygen or sulfur.

The halogen is fluorine, chlorine or bromine.

According to the present invention, the preferred embodiment A of the compound represented by the formula (I) is compound of the general formula (I) wherein Ar is represented by:

the formula (a):

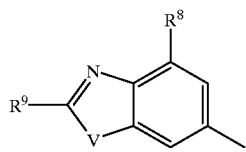

(a)

wherein $R^8$, $R^9$ and V have the same meaning as defined for $R^8$, $R^9$ and V in the formula (A); or the formula (b):

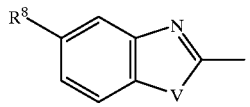

(b)

wherein $R^8$, W and X have the same meaning as defined above for $R^8$, W and X in the formula (B); or the formula (c):

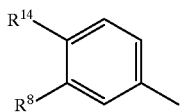

(c)

wherein $R^8$ and $R^{14}$ have the same meaning as defined above for $R^8$ and $R^{14}$ in the formula (C).

The preferred embodiment B of the present compound is a compound of the formula (I) wherein Ar is represented by the formula (C) wherein $R^{14}$ is represented by the $R^{14'}$ wherein Y is oxygen atom, and Z is represented by the formula:

wherein $R^{18}$ and $R^{19}$ together form a 3 to 7-membered ring. More preferably, Z is represented by the formula:

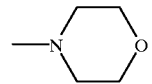

The preferred embodiment C of the present compound is a compound of the formula (I) wherein Ar is represented by the formula (C) wherein $R^{14}$ is represented by the $R^{14'}$ in which Y is N—$R^{15}$, and Z is —$OR^{16}$ wherein $R^{15}$ and $R^{16}$ together form a 3 to 7-membered ring. Preferably Y(N—$R^{15}$) and Z(—$OR^{16}$) together form the formula:

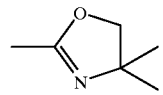

The preferred embodiment D of the present compound is a compound of the formula (I) wherein $R^1$, $R^2$ and $R^3$ are independently an alkyl group, and preferably a lower alkyl group and more preferably a lower alkyl group having 1 to 4 carbon atoms, such as tert-butyl group; and each of $R^4$, $R^5$, $R^6$ and $R^7$ is preferably a hydrogen atom.

In the preferred embodiment A, the substituents other than Ar may have the same meanings as defined for the corresponding substituents in the general formula (I). In the preferred embodiment B, the substituents other than Ar and $R^8$ in the formula (C) may have the same meanings as defined for the corresponding substituents in the general formula (I). In the preferred embodiment C, the substituents other than Ar and $R^4$ in the formula (C) may have the same meanings as defined for the corresponding substituents in the general formula (I).

Alternatively, and most preferably, the present compound is represented by the formula (I) wherein Ar is represented as defined in the preferred embodiments A, B or C, and the substituents other than Ar are those defined in the preferred embodiment D.

The 1,2-dioxetane derivative represented by the general formula (I) of the present invention can be produced from a dihydropyran ring derivative having an aryl group substituted with $R^{81}$, which is represented by the general formula:

(II)

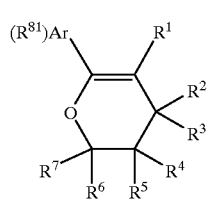

wherein $R^1$ to $R^7$ have the same meaning as defined for $R^1$ to $R^7$ in the general formula (I); $R^{81}$ is an alkoxyl group or an aralkyloxy group; and ($R^{81}$)Ar is a group represented by:

the formula (A'):

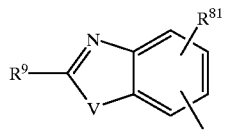

wherein $R^9$ and V have the same meaning as $R^9$ and V in the formula (A); and $R^{81}$ has the same meaning as in the general formula (II);

the formula (B'):

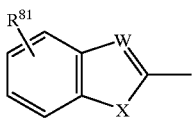

wherein W and X have the same meaning as W and X in the formula (B); and $R^{81}$ has the same meaning as $R^{81}$ in the general formula (II); or the formula (C'):

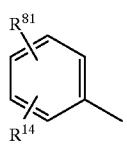

wherein $R^{14}$ has the same meaning as $R^{14}$ in the formula (C); and $R^{81}$ has the same meaning as $R^{81}$ in the general formula (II), in accordance with the following reaction scheme A.

Reaction Scheme A

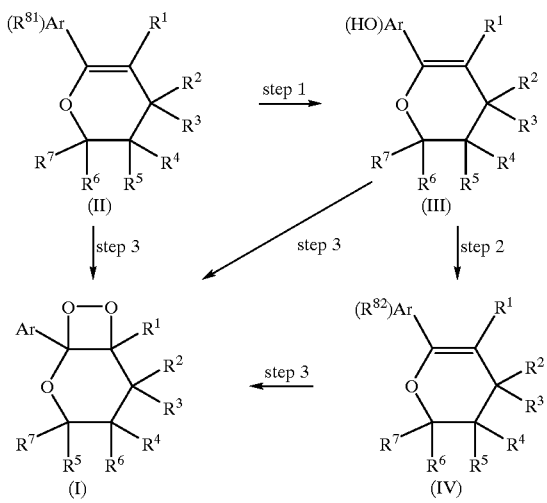

In the reaction scheme A, $R^1$ to $R^7$ have the same meaning as those in the general formula (I); $R^{81}$ has the same meaning as that in the general formula (II); $R^{82}$ is a phosphoric group represented by the formula:

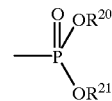

(wherein $R^{20}$ and $R^{21}$ represent an alkyl group, or $R^{20}$ and $R^{21}$ may together form a ring) or a group represented by —OSi($R^{10}R^{11}R^{12}$) ($R^{10}$, $R^{11}$ and $R^{12}$ are as defined above; a group-represented by (HO)Ar— in the general formula (III) has an OH group at the same position as that of the substituent $R^{81}$ in the general formula (II); and a group represented by ($R^{82}$)Ar of the general formula (IV) has $R^{82}$ at the same position as that of the substituent $R^{81}$ in the general formula (II).

In the above description, the alkoxy and aralkyloxy groups have the same meanings as defined for $R^8$ in the formula (A).

Step 1

In this step, a deblocking reaction of the compound represented by the general formula (II) is effected to produce a compound represented by the general formula (III).

The compound to be subjected to the deblocking reaction is a compound represented by the general formula (II) (wherein $R^1$ to $R^7$ are as defined above; and $R^{81}$ is an alkyl group or an aralkyl group (preferably a methoxy group or a benzyloxy group), and this reaction can be effected by a procedure which is well known to a person with an ordinary skill in the art, that is, reaction of anions of an alkylthiol or hydrogenation reaction, which may be appropriately selected according to the group to be deblocked.

Step 2

In this step, the compound represented by the general formula (III) is reacted with a corresponding halogenated trialkylsilane or halogenated phosphate for forming a silyloxy group or a phosphoric group, thereby to produce a compound represented by the general formula (IV).

In this step, when chloroethylene phosphate is reacted to introduce a phosphoric group, the reaction product can be converted into a sodium salt of cyanoethyl phosphate using sodium cyanate, which can be further converted into an ammonium sodium salt by eliminating a cyanoethyl group. This ammonium sodium salt can be easily converted into a disodium salt by reacting with sodium hydrogencarbonate.

Step 3

In this step, the compound represented by the general formula (II), (III) or (IV) is reacted with a singlet oxygen to produce a 1,2-dioxetane derivative represented by the general formula (I).

The reaction with the singlet oxygen is attained by irradiating a dihydropyran derivative represented by the general formula (II), (III) or (IV) with visible light under an oxygen atmosphere in the presence of a photosensitizer such as methylene blue, rose bengal, or tetraphenylporphine (TPP).

In this reaction, a halogenated hydrocarbon such as dichloromethane, dichloroethane, or carbon tetrachloride; and an alcohol such as methanol or ethanol can be used as the solvent.

The reaction is preferably effected at −80° C. to room temperature.

The method of producing the dihydropyran derivative represented by the general formula (II) includes, for example, the following method.

(1) Case wherein the ($R^{81}$)Ar is a group represented by the formula (A')

In the case wherein the ($R^{81}$)Ar is a group represented by the formula (A') in the compound represented by the general formula (II), the dihydropyran derivative represented by the general formula (II) can be produced in accordance with the following reaction scheme B:

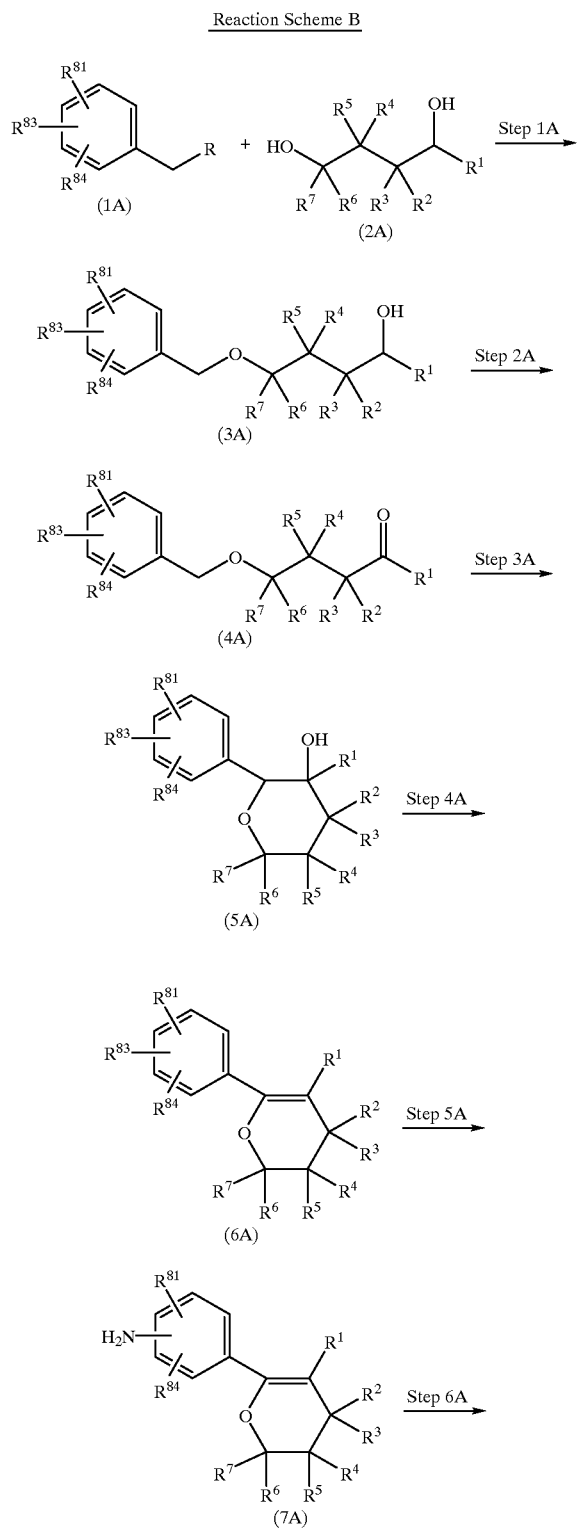

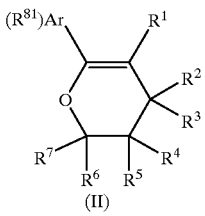

In the reaction scheme B, $R^1$ to $R^7$ and $R^{81}$ have the same meaning as defined above; $R^{83}$ is halogen atom; $R^{84}$ is an alkoxyl group or an aralkyloxy group ($R^{83}$ and $R^{84}$ are combined with adjacent carbon atoms); R is halogen atom, a substituted sulfonyloxy group, or a hydroxyl group; and $(R^{81})Ar$ of the compound represented by the general formula (II) is a group represented by the formula (A').

Step 1A

In this step, a compound represented by the general formula (1A) is reacted with a compound represented by the general formula (2A) to produce a compound represented by the general formula (3A).

The reaction can be attained by so-called Williamson synthesis which is well known to a person with an ordinary skill in the art.

When a substituent R of the compound represented by the general formula (1A) is halogen atom or a substituted sulfonyloxy group, this step can be attained by directly subjecting the compound to the reaction. On the other hand, when X is a hydroxyl group, this step can be attained by subjecting the compound to the reaction after the hydroxyl group into a sulfonyloxy group in the reaction system using halogenated tosyl.

Step 2A

In this step, the compound represented by the general formula (3A) is oxidized to produce a compound represented by the general formula (4A).

Oxidation in this step can be effected by using a chromium-based oxidizing agent or an activator.

As a chromium-based oxidizing agent, for example, pyridinium chloroformate (PCC) or pyridinium dichlorochromate (PDC) can be used. As a solvent, for example, a halogenated hydrocarbon such as dichloromethane can be used.

When using the activator, the reaction can be effected by using a combination with a solvent such as Py.SO$_3$/triethylamine/DMSO or Ac$_2$O/DMSO.

Step 3A

In this step, a compound represented by the general formula (5A) is produced by ring-formation of the compound represented by the general formula (4A).

The reaction is effected by using a lithium salt of a secondary amine, such as lithium diisopropylamide, or a base such as t-butoxypotassium.

As the solvent, for example, an organic solvent such as THF or DMSO can be used. The reaction is preferably effected at 0° C. to room temperature for 1 to 5 hours.

Step 4A

In this step, the compound represented by the general formula (5A) is dehydrated to produce a compound represented by the general formula (6A).

The reaction can be effected by reacting with thionyl chloride in the presence of a base such as pyridine, or by using, as a catalyst, an acid such as phosphoric acid or p-toluenesulfonic acid.

As the solvent, for example, a halogenated hydrocarbon such as methylene chloride, or an aromatic hydrocarbon such as toluene can be used. The solvent can be appropriately selected according to a reagent to be reacted.

Step 5A

In this step, the compound represented by the general formula (6A) is reduced to produce a compound represented by the general formula (7A).

The reaction can be attained by reacting with a lithium salt such as butyllitium, reacting with an azide such as p-toluenesulfonazide, reducing with triphenyl phosphine, and reacting with a thiol such as ethanethiol.

As the solvent, for example, an organic solvent such as DMF can be used. The reaction is preferably effected under reflux.

Step 6A In this step, a compound represented by the general formula (II) is produced from the compound represented by the general formula (7A).

The reaction can be effected by converting $R^{84}$ of the compound represented by the general formula (7A) into a hydroxyl group or a SH group, and reacting with an orthocarboxylic acid ester or carbonylimidazole, thereby making it possible to form a condensed ring.

When using the orthocarboxylic acid ester, the reaction is preferably effected under heating at 100 to 200° C. When using carbonylimidazole, the reaction is preferably effected at 0° C. to room temperature.

(2) Case wherein the $(R^{81})Ar$ is a group represented by the formula (C')

In case $(R^{81})Ar$ is a group represented by the formula (C') in the compound represented by the general formula (II), the dihydropyran derivative represented by the general formula (II) can be obtained in accordance with the following reaction scheme C:

Reaction Scheme C

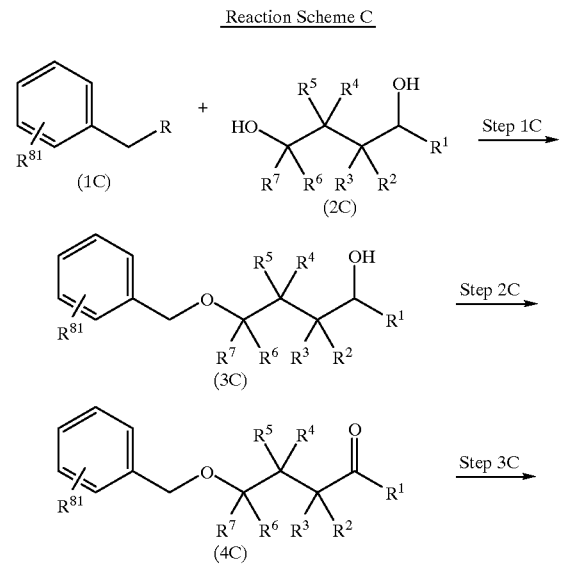

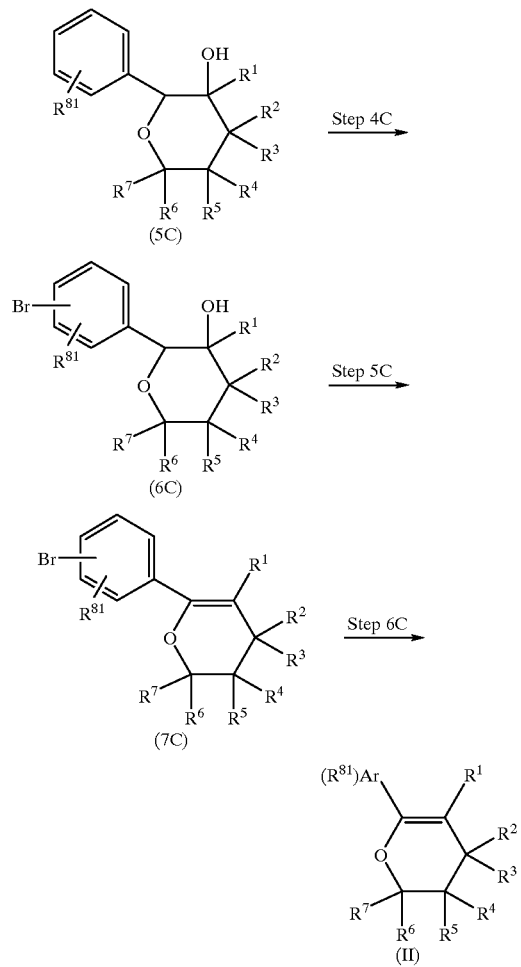

In the reaction scheme C, $R^1$ to $R^7$, $R^{81}$ and R have the same meaning as defined above; and $(R^{81})Ar$ in the compound represented by the general formula (II) is a group represented by the formula (C').

Step 1C

In this step, a compound represented by the general formula (1C) is reacted with a compound represented by the general formula (2C) to produce a compound represented by the general formula (3C).

The compound represented by the general formula (2C) is the same as the compound represented by the general formula (2A) used in case $(R^{81})Ar$ is a group represented by the formula (A'). This step 1C can be attained by Williamson synthesis in the same manner as in the step 1A.

Steps 2C and 3C

The method of producing a compound represented by the general formula (5C) through these steps can be attained in the same manner as in the steps 2A and 3A.

Step 4A

In this step, the compound represented by the general formula (5C) is brominated to produce a compound represented by the general formula (6C).

The reaction is attained by using a brominating agent such as N-bromosuccinimide. As the solvent, for example, an organic solvent such as hydrous THF, dioxane, or DMF can be used.

Step 5C

This step can be effected in the same manner as in the step 4A.

In this step, bromine of a compound represented by the general formula (7C) is substituted to produce a compound represented by the general formula (II) into which a desired substituent is introduced.

Introduction of a substituted amino group can be effected by introducing a carboxyl group using a lithium salt such as butyllithium, and reacting with an amine or ammonia using carbonylimidazole as a condensing agent.

The amide produced by the above reaction can be converted into a compound having an oxazoline ring by reacting with a substituted or non-substituted ethanolamine.

Introduction of an acyl group can be attained by reacting with N-methylformanilide using a lithium salt such as butyllithium in the same manner as described above, or reacting with an aldehyde such as acetaldehyde or benzaldehyde and oxidizing a hydroxyl group using an oxidizing agent such as manganese dioxide.

The compound into which the acyl group has been introduced is converted into an oxime by subjecting to the step 1 and reacting with a hydroxylamine or alkoxylamine, and the oxime can be used as a starting material of the step 3.

(3) Case wherein the $(R^{81})Ar$ is a group represented by the formula (B')

In case wherein the $(R^{81})Ar$ is a group represented by the formula (B') in the compound represented by the general formula (II), the dihydropyran derivative represented by the general formula (II) can be obtained in accordance with the following reaction scheme D.

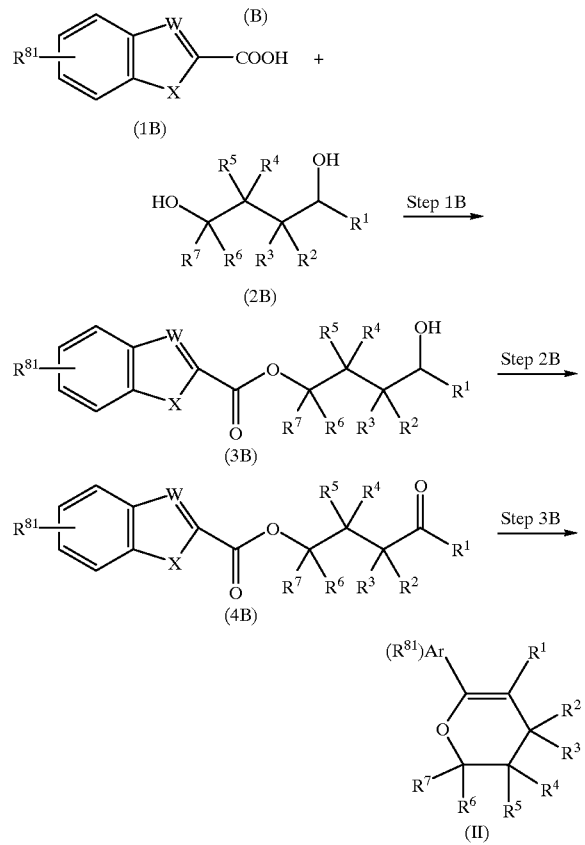

In the reaction scheme D, $R^1$ to $R^7$, W, X and $R^{81}$ have the same meaning as defined above; and $(R^{81})Ar$ of the compound represented by the general formula (II) is a group represented by the formula (B').

Step 1B

In this step, a compound represented by the general formula (1B) is condensed with a compound represented by the general formula (2B) to produce a compound represented by the general formula (3B).

The reaction can be effected in the presence of a condensing agent. The condensing agent includes, for example, carbodiimide or carbonylimidazole.

When the reaction is effected, a halogenated hydrocarbon such as dichloromethane can be used as the solvent.

Step 2B

This step is effected in the same manner as in the above step 2A.

Step 3B

In this step, an alcohol derivative is produced from a compound represented by the general formula (4B) using a reducing agent and a base in the presence of titanium, and then the alcohol derivative is subjected to a cyclodehydration reaction in the presence of an acid catalyst to produce a compound represented by the general formula (II).

It is an indispensable feature for the pre-stage reaction to be effected in the presence of titanium. Halogenated titanium such as titanium chloride is preferably used as titanium. The reaction is preferably effected after the reduced state is attained by using aluminum lithium hydride as a reducing agent and using triethylamine or pyridine as a base. The reaction is preferably effected in an organic ether such as THF. The reaction proceeds at 0 to 100° C., but is preferably effected under reflux of THF in view of the operation and reactivity.

In the post-stage cyclodehydration reaction, PPTS or p-toluenesulfonic acid is preferably used as an acid catalyst. The reaction can be effected by using a halogenated hydrocarbon or an aromatic hydrocarbon such as benzene or toluene as a solvent.

The 1,2-dioxetane derivative represented by the general formula (I) of the present invention is not only discomposed with accompanying a chemiluminescence under alkali conditions to form a carbonyl compound, but also decomposed with accompanying a chemiluminescence by an enzyme, for example, esterase (carboxylic acid ester hydrolase) such as arylesterase or acetylcholinesterase, or acidic or alkali phosphatase. Accordingly, the 1,2-dioxetane derivative can be not only used as a reagent in an immunoassay for the purpose of determining the concentration of a substance to be detected in the sample, but also used as a labeled reagent.

The substances to be detected in the immunoassay, includes, for example, hormones such as hCG, TSH, or LH; carcinogens such as AFP or CEA; and virus antigen such as HIV or HTLV-1, and an antibody or a nucleic acid thereof.

According to the above immunoassay, the following steps are included: the step of providing a conjugate consisting of the enzyme and a substance having a specific binding property to the above substance to be detected, mixing and reacting the conjugate with a sample containing the substance to be detected for a fixed time, and the step of determining the amount of the enzyme of the conjugate which has been bound or not bound to the substance to be detected in the sample by means of measuring the intensity of chemiluminescence of the product of the enzyme reaction with the substrate 1,2-dioxetane derivative. The amount of the enzyme indicates the concentration of the substance to be detected.

The reagent for immunoassay, comprising the 1,2-dioxetane derivative of the present invention, and the above-described immunoassay using the same are also included in the present invention.

The 1,2-dioxetane represented by the general formula (I) of the present invention is a compound which has a high thermal stability and a very high light emission quantum efficiency. Accordingly, the compound can be stored for a long period of time without being refrigerated, and the same object can be attained using a small amount of the compound as compared with a conventional compound because of good light emission efficiency. When using it in the field of clinical analysis, the substance to be detected can be detected in an efficient and simple manner.

EXAMPLES

The following Examples and Reference Examples further illustrate the present invention in detail.

Reference Example 1

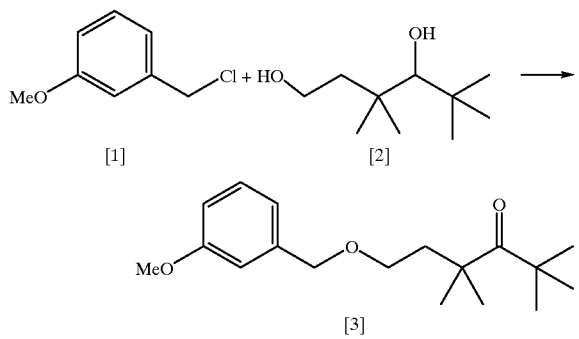

Under a nitrogen atmosphere, 584 mg (14.4 mmol) of 60% sodium hydride was added to 10 mL of DMF. The solution was cooling to 0° C. and a solution prepared by dissolving 2.09 g (12.0 mmol) of 3,3,5,5-tetramethyl-1,4-hexanediol (compound [1]) in 5 ml of DMF was added dropwise, followed by stirring for 30 minutes. A solution prepared by dissolving 1.75 mL (12.1 mmol) of 3-methoxybenzyl chloride (compound [2]) in 3 mL of DMF was added dropwise, followed by cooling to room temperature and further stirring overnight. The reaction solution was poured into a saturated ammonium chloride solution and then extracted with ethyl acetate. The aqueous layer was extracted with ethyl acetate and combined with the organic layer obtained previously, and then the combined layer was washed with a saturated sodium chloride solution three times. The organic layer was concentrated by drying over magnesium sulfate. The concentrate was eluted by subjecting to silica gel column using a mixed solvent of ethyl acetate and hexane (1:5) as an eluent to obtain 3.08 g of 6-(3-methoxy)benzyloxy-2,2,4,4-tetramethyl-3-hexanol as a colorless oily product (yield: 87.1%).

2.63 g (8.93 mmol) of the resulting 6-(3-methoxy) benzyloxy 2,2,4,4-tetramethyl-3-hexanol was dissolved in 10 mL of methylene chloride and the solution was added dropwise in a mixed solution of 30 mL of methylene chloride, 2.64 g (12.2 mmol) of PCC and 7.69 g of celite under a nitrogen atmosphere, followed by stirring overnight. To the reaction solution, 5 mL of 2-propanol and 120 mL of ether were added, followed by stirring for one hour. Then, the mixture was filtered with celite and the filtrate was concentrated. The concentrate was eluted by subjecting it to a silica gel column using a mixed solvent of ethyl acetate and hexane (1:7) as an eluent to obtain 2.46 g of 6-(3-methoxy)benzyloxy-2,2,4,4-tetramethyl-3-hexanol (compound [3]) as a colorless oily product (yield: 94.3%).

$^1$HNMR (400 MHz, CDCl$_3$); δ1.22 (s, 9H), 1.27 (s, 6H), 1.96 (t, J=7.0 Hz, 2H), 3.39 (t, J=7.0 Hz, 2H), 3.81 (s, 3H), 4.42 (s, 2H), 6.81 (d with fine coupling, J=8.9 Hz, 1H), 6.86–6.88 (m, 2H) ppm.

Reference Example 2

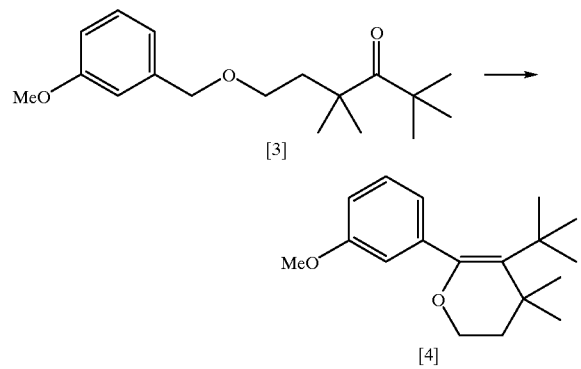

Under a nitrogen atmosphere, 2.10 mL (15.0 mmol) of diisopropylamine was added to 15 mL of THF at room temperature and 8.50 mL (13.7 mmol) of 1.60M butyllithium was added, followed by stirring for 30 minutes. The mixture was cooling to −78° C. and a solution prepared by dissolving 2.27 g (7.76 mmol) of 6-(3-methoxy)benzyloxy-2,2,4,4-tetramethyl-3-hexanone (compound [3]) in 5 mL of THF, was added dropwise. The reaction solution was generally cooled to room temperature, and then stirred for three hours. The reaction solution was poured into a saturated ammonium chloride solution and then extracted with ethyl acetate. The aqueous layer was extracted with ethyl acetate and combined with the organic layer obtained previously, and then the combined layer was washed with a saturated sodium chloride solution three times. The organic layer was concentrated by drying over magnesium sulfate. The concentrate was eluted by subjecting to silica gel column using a mixed solvent of ethyl acetate and hexane (1:7) as an eluent to obtain 2.08 g of 3-t-butyl-3-hydroxy-2-(3-methoxy)phenyl-4,4-dimethyl-3,4,5,6-tetrahydropyran as a colorless oily product (yield: 91.8%).

Under a nitrogen atmosphere at room temperature, 1.74 g (5.96 mmol) of the resulting 3-t-butyl-3-hydroxy-2-(3-methoxy)phenyl-4,4-dimethyl-3,4,5,6-tetrahydropyran and 5.5 mL (68.0 mmol) of pyridine were added to 20 mL of methylene chloride. The mixture was cooled to 0° C. and 0.75 mL (10.3 mmol) of thionyl chloride was added, followed by stirring for two hours. The reaction solution was poured into a saturated sodium chloride solution and extracted with ethyl acetate. The aqueous layer was extracted with ethyl acetate and combined with the organic layer obtained previously, and then the combined layer was washed with a saturated sodium chloride solution three times. The organic layer was concentrated by drying over magnesium sulfate. The concentrate was eluted by subjecting it to a silica gel column using a mixed solvent of methylene chloride and hexane (2:1) as an eluent to obtain 1.25 g of 5-t-butyl-6-(3-methoxy)phenyl-4,4-dimethyl-3,4-dihydropyran (compound [4]) as a colorless oily product (yield: 76.7%).

$^1$HNMR (400 MHZ, CDCl$_3$); δ1.04 (S, 9H), 1.39 (s, 9H), 1.39 (s, 6H), 1.69 (t, J=5.2 Hz, 2H), 3.80 (s, 3H), 4.01 (t,

J=5.2 Hz, 2H), 6.83–6.87 (m, 3H), 4.01 (t, J=5.2 Hz, 2H), 6.83–6.87 (m, 3H), 7.21 (t, J=7.8 Hz, 1H) ppm.

IR (liquid film); 2924, 2856, 1585, 1238, 1047 cm$^{-1}$.

Mas (m/z, %); 259 (36), 218 (27), 203 (100), 151 (24), 135 (30), 111 (26), 77 (51).

Example 1

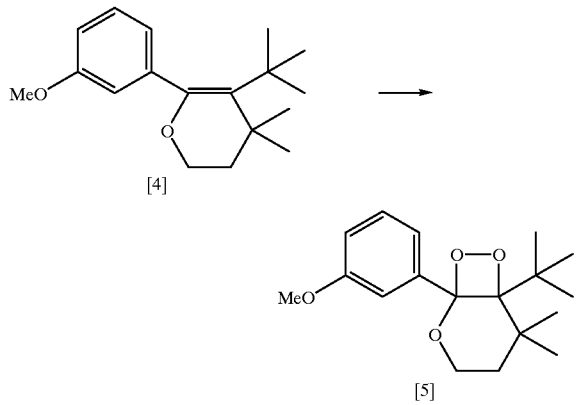

Under an oxygen atmosphere at 0° C., 70.7 mg (0.258 mmol) of 5-t-butyl-6-(3-methoxy)phenyl-4,4-dimethyl-3,4-dihydropyran (compound [4]) and 1.3 mg of TPP were added to 5 mL of bichloroform and the mixture was externally irradiated for eight hours using a 940 W sodium lamp. The reaction solution was concentrated and then eluted by subjecting to silica gel column using a mixed solvent of ether and hexane (1:20) as an eluent to obtain 45.7 mg of 6-t-butyl-1-(3-methoxy)phenyl-5,5-dimethyl-2,7,8-trioxabicyclo[4.2.0]octane (compound [5]) as a colorless oily product (yield: 57.9%).

Melting point; 107–108° C.

$^1$HNMR (400 MHZ, CDCl$_3$); δ0.99 (s, 9H), 1.17 (s, 3H), 1.37–1.44 (m, 1H), 1.54 (s, 3H), 3.01 (dt, J=13.2 and 9.7 Hz, 1H), 3.81 (s, 3H), 4.11 (q, J=9.7Hz, 1H), 4.40–4.45 (m, 1H), 6.80–7.29 (m, 4H) ppm.

IR (KBr); 2972, 2898, 1612, 1291, 1091 cm$^{-1}$.

Reference Example 3

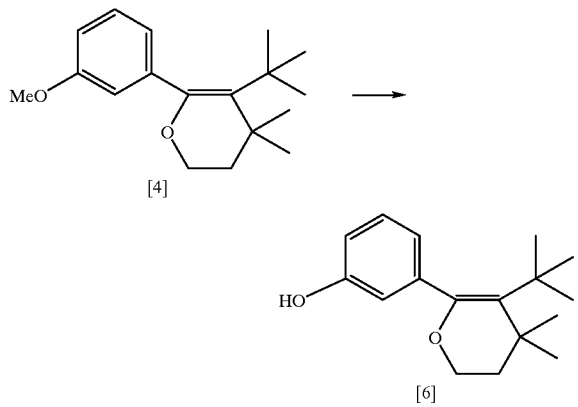

Under a nitrogen atmosphere at 0° C., 153 mg (1.31 mmol) of 60% sodium hydride was added to 2 mL of DMF and 0.12 mL (1.55 mmol) of ethanethiol was then added, followed by stirring. A solution prepared by dissolving 171 mg (0.62 mmol) of 5-t-butyl-6-(3-methoxy)phenyl-4,4-dimethyl-3,4-dihydropyran (compound [4]) in 2 mL of DMF was added dropwise and the mixture was refluxed for two hours. The reaction solution was poured into a saturated sodium chloride solution and extracted with ethyl acetate. The aqueous layer was extracted with ethyl acetate and combined with the organic layer obtained previously, and then the combined layer was washed with a saturated sodium chloride solution three times. The organic layer was concentrated by drying over magnesium sulfate. The concentrate was eluted by subjecting it to a silica gel column using a mixed solvent of ethyl acetate and hexane (1:5) as an eluent to obtain 131 mg of 5-t-butyl-6-(3-hydroxy)phenyl-4,4-dimethyl-3,4-dihydropyran (compound ([6]) as a colorless oily product (yield: 80.7%).

Melting point; 131–132° C.

$^1$HNMR (400 MHz, CDCl$_3$); δ1.04 (s, 9H), 1.39 (s, 6H), 1.68 (t, J=5.3 Hz, 2H), 4.00 (t, J=5.3 Hz, 2H), 4.62 (s, 1H), 6.74–6.76 (m, 2H), 6.85 (d, J=7.7 Hz, 1H), 7.17 (t, J=7.7 Hz, 1H) ppm.

IR (KBr); 3401, 2963, 2881, 1588, 1442, 1112 cm$^{-1}$

Mass (m/z, %); 245 (23), 204 (25), 189 (100), 175 (3), 121 (22), 93 (6).

Reference Example 4

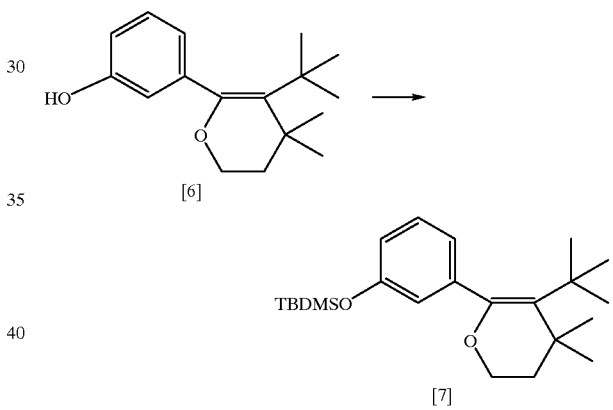

Under a nitrogen atmosphere at room temperature, 92.7 mg (0.356 mmol) of 5-t-butyl-6-(3-hydroxy)phenyl-4,4-dimethyl-3,4-dihydropyran (compound [6]) and imidazole (60 mg, 0.881 mmol) were added to 3 mL of DMF. Then, 102 mg (0.679 mmol) of t-butyldimethylchlorosilane was added, followed by stirring for two hours. The reaction solution was poured into a saturated sodium chloride solution and extracted with ethyl acetate. The aqueous layer was extracted with ethyl acetate and combined with the organic layer obtained previously, and then the combined layer was washed with a saturated sodium chloride solution three times. The organic layer was concentrated by drying over magnesium sulfate. The concentrate was eluted by subjecting to silica gel column using a mixed solvent of ethyl acetate and hexane (1:10) as an eluent to obtain 114 mg of 5-t-butyl-6-(3-t-butyldimethylsiloxy)phenyl-4,4-dimethyl-3,4-dihydropyran (compound [7]) as a colorless oily product (yield: 85.6%).

$^1$HNMR (400 MHz, CDCl$_3$); δ0.17 (s, 6H), 0.98 (s, 9H), 1.03 (s, 9H), 1.38 (s, 6H), 1.68 (t, J=5.3 Hz, 2H), 4.00 (t, J=5.3 Hz, 2H), 6.74–6.76 (m, 2H), 6.85 (d, J=7.6 Hz, 1H), 7.14 (t, J=7.6 Hz, 1H) ppm.

IR (liquid film); 2956, 2880, 1582, 1242, 1043, 850 cm$^{-1}$.

Mass (m/z, %); 375 (M$^+$, 5), 359 (83), 318 (38), 252 (18), 203 (7), 151 (17).

Example 2

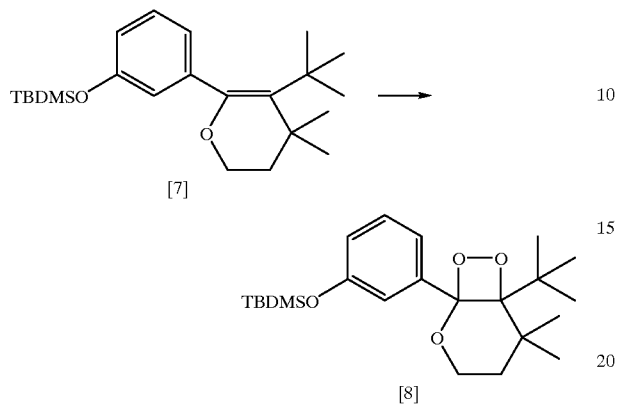

Under an oxygen atmosphere at 0° C., 95.1 mg (0.234 mmol) of 5-t-butyl-6-(3-t-butyldimethylsiloxy)phenyl-4,4-dimethyl-3,4-dihydropyran (compound [7]) and 1.2 mg of TPP were added to 10 mL of bichloroform and the mixture was externally irradiated for eight hours using a 940 W sodium lamp. The reaction solution was concentrated and then eluted by subjecting to silica gel column using a mixed solvent of ether and hexane (1:30) as an eluent to obtain 93.0 mg of 6-t-butyl-1-(3-t-butyldimethylsiloxy)phenyl-5,5-dimethyl -2,7,8-trioxabicyclo[4.2.0]octane (compound [8]) as a colorless oily product (yield: 73.8%).

$^1$HNMR (400 MHz, CDCl$_3$); δ0.18 (s, 6H), 0.98 (s, 9H), 0.99 (s, 9H), 1.37–1.43 (m, 1H), 1.58 (s, 3H), 3.00 (dt, J=13.2 and 9.5 Hz, 1H), 4.07–4.14 (m, 1H), 4.39–4.45 (m, 1H), 6.79–7.15 (m, 2H), 7.21 (t, J=8.1 Hz, 2H) ppm IR (liquid film); 2957, 2860, 1598, 1125, 1057 cm$^{-1}$.

Reference Example 5

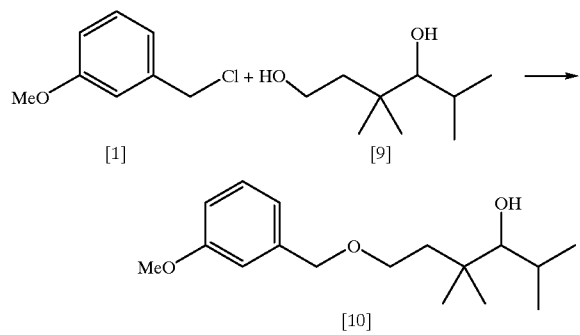

Under a nitrogen atmosphere, 1.48 mg (36.90 mmol) of 60% sodium hydride was added to 30 mL of THF and a solution prepared by dissolving 3.07 g (30.75 mmol) of 3,3,5-trimethyl 1,4-hexanediol (compound [9]) in 10 mL of THF was then added under ice cooling and, after stirring for 30 minutes, 4.47 mL (30.75 mmol) of m-methoxybenzyl chloride (compound [2]) was added, followed by stirring for additional 30 minutes. 10 mL of DMF was added, and then 10 mL of DMF was added after two hours. The reaction solution was extracted with ethyl acetate, washed in turn with an aqueous saturated ammonium chloride solution and a saturated sodium chloride solution, and then concentrated by drying over magnesium sulfate. The concentrate was eluted by subjecting it to a silica gel column using a mixed solvent of hexane and ethyl acetate (7:1) as an eluent to obtain 5.41 g of 6-(3-methoxybenzyloxy)-2,3,3-trimethyl-3-hexanol (compound [10]) as a yellow oily product (yield: 62.7%).

$^1$HNMR (400 MHz, CDCl$_3$); δ0.90 (s, 3H), 0.93 (s, 3H), 0.93 (t, J=7.1 Hz, 3H), 1.00 (d, J=7.1 Hz, 3H), 1.67 (q$_{AB}$t, J=14.7 and 5.4 Hz, 2H), 1.81–1.94 (m, 1H), 2.87 (d, J=5.9 Hz, 1H), 3.15 (dd, J=5.9 and 1.0 Hz, 1H), 3.81 (s, 3H), 3.50–3.59 (m, 2H), 4.50 (q$_{AB}$t, J=12.1 Hz, 2H), 6.83 (dd, J=8.3 and 2.4 Hz, 1H), 6.89 (s, 1H), 6.90 (d, J=11.2 Hz, 1H), 7.25 (t, J=7.8 Hz, 1H) ppm IR (liquid film); 3447, 2958, 2871, 1467, 1266, 783, 743 cm$^{-1}$.

Reference Example 6

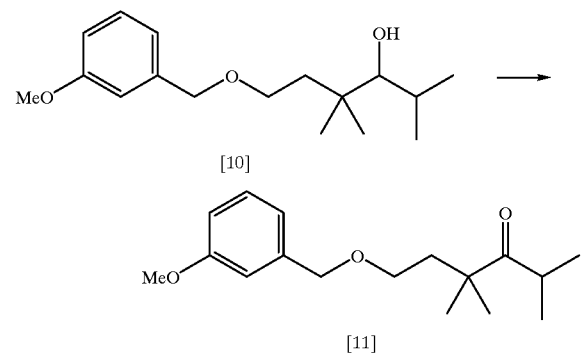

Under a nitrogen atmosphere, 24.28 g of celite, 12.14 g (56.25 mmol) of PCC and a solution prepared by dissolving 10.53 g (37.55 mmol) of 6-(3-methoxybenzyloxy)-2,3,3-trimethyl-3-hexanol (compound [10]) in 5 mL of methylene chloride were added to 80 mL of methylene chloride, followed by stirring overnight. 9.92 ml (0.13 mmol) of isopropanol was added and, after 60 minutes, ether was added, followed by stirring for 10 minutes. Then, the mixture was filtered with celite and the filtrate was concentrated. The concentrate was eluted by subjecting to silica gel column using a mixed solvent of hexane and ethyl acetate (5:1) as an eluent to obtain 9.85 g of 6-(3-methoxybenzyloxy)-2,3,3-trimethyl-3-hexanone (compound [11]) as a colorless oily product (yield: 90.6%).

$^1$HNMR (400 MHz, CDCl$_3$ ); δ1.02 (d, J=6.36 Hz, 6H), 1.16 (s, 6H), 1.89 (t, J=7.1 Hz, 2H), 3.11 (hept, J=6.8 Hz, 1H), 3.41 (t, J=6.8 Hz, 2H), 3.82 (s, 3H), 4.43 (s, 2H), 6.81 (d with fine coupling, J=8.3 Hz, 1H), 6.86–6.86 (m, 2H), 7.24 (t, J=8.5 Hz, 1H) ppm.

IR (liquid film); 2968, 2871, 1702, 1490, 1266, 1050, 743 cm$^{-1}$.

Reference Example 7

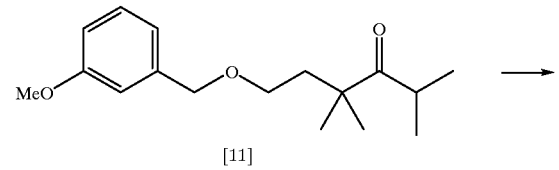

21

-continued

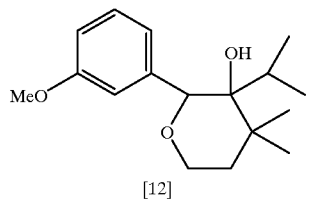

[12]

Under a nitrogen atmosphere, 4.67 mL (0.033 mol) of diisopropylamine and 20.01 mL (0.032 mol) of butyllithium were added to 25 mL of THF, followed by stirring for 30 minutes. After cooling to −78° C., a solution prepared by dissolving 3.00 (0.011 mol) of 6-(3-methoxybenzyloxy)-2,3,3-trimethyl-3-hexanone (compound [11]) in 10 mL of THF was added dropwise, followed by stirring at −78° C. for three hours, heating to −25° C. and further stirring for additional two hours and a half. The reaction solution was extracted with ethyl acetate, washed in turn with an aqueous saturated ammonium chloride solution and a saturated sodium chloride solution, and then concentrated by drying over magnesium sulfate. The concentrate was eluted by subjecting it to a silica gel column using a mixed solvent of ethyl acetate and hexane (1:5) as an eluent, and then eluted by subjecting it again to a silica gel column using a mixed solvent of hexane and methylene chloride (2:3) to obtain 1.09 g of 3-hydroxy-3-isopropyl-2-(3-methoxyphenyl)-4,4-dimethyl-2,3,4,5-tetrahydropyran (compound [12]) as a colorless oily product (yield: 70.41).

Melting point; 56.0–56.90° C. (columnar crystal, recrystallized from hexane).

$^1$HNMR (400 MHz, CDCl$_3$); δ1.02 (d, J=7.3 Hz, 3H), 1.13 (s, 3H), 1.15 (s, 1H), 1.19 (d, J=7.3 Hz, 6H), 1.19–1.26 (m, 1H), 1.27 (s, 3H), 1.73 (sept, J=7.16, 1H), 2.30 (td, J=13.4 and 5.9 Hz, 1H), 3.81 (s, 3H), 3.89 (ddd, J=13.4, 11.7 and 2.9 Hz, 1H), 3.99 (dd, J=11.7 Hz and 5.9 Hz, 1H), 4.68 (s, 1H), 6.81 (d with fine coupling, J=8.3 Hz, 1H), 7.01 (d, J=7.8 Hz, 1H), 7.02 (s, 1H), 7.23 (t, J=7.8 Hz, 1H) ppm.

$^{13}$CNMR (100 MHz, CDCl$_3$); δ19.9, 20.5, 25.1, 27.7, 34.7, 39.1, 39.3, 55.2, 64.8, 75.8, 83.6, 112.9, 119.9, 128.7, 141.2, 159.3 ppm.

IR (KBr); 3514, 2971, 2861, 1601, 1491, 1173, 1019, 707 cm$^{-1}$.

Reference Example 8

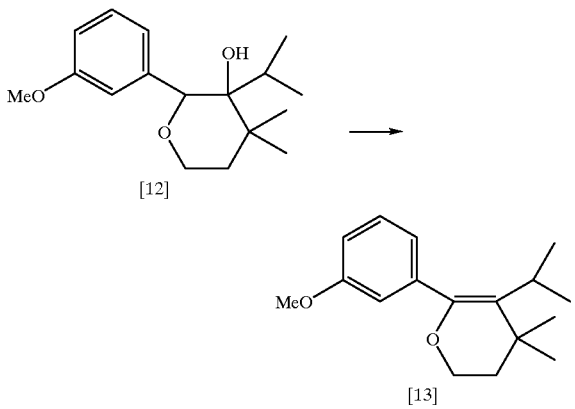

Under a nitrogen atmosphere, 2.91 mL (35.92 mmol) of pyridine and 1.01 g (3.59 mmol) of 3-hydroxy-3-isopropyl-2-(3-methoxyphenyl)-4,4-dimethyl-2,3,4,5-tetrahydropyran (compound [12]) were added to 10 mL of anhydrous methylene chloride and 0.34 mL (4.67 mmol) of thionyl chloride was added at 0° C., followed by stirring overnight. The reaction solution was extracted with ethyl acetate, washed in turn with an aqueous saturated ammonium chloride solution and a saturated sodium chloride solution, and then concentrated by drying over magnesium sulfate. The concentrate was eluted by subjecting to silica gel column using a mixed solvent of ethyl acetate and hexane (1:7) as an eluent to obtain 0.71 g of 5-isopropyl-6-(3-methoxyphenyl)-4,4-dimethyl-2,3-dihydropyran (compound [13]) as a colorless oily product (yield: 71.27%). $^1$HNMR (400 MHz, CDCl$_3$); δ0.90 (d, J=7.32 Hz, 6H), (1.19 (s, 6H), 1.73 (t, J=5.4 Hz, 2H), 2.43 (hept, J=7.3 Hz, 1H), 3.81 (s, 3H), 4.04 (t, J=5.1 Hz, 2H), 6.83–6.89 (m, 3H), 7.23 (t, J=7.8 Hz, 1H) ppm.

$^{13}$CNMR (100 MHz, CDCl$_3$); δ24.0, 27.4, 28.8, 32.6, 39.9, 55.1, 62.8, 113.6, 115.6, 122.0, 122.7, 128.6, 139.9, 148.4, 158.9 ppm.

IR (liquid film); 2958, 2932, 2870, 1464, 1241, 1048, 789 cm$^{-1}$.

Example 3

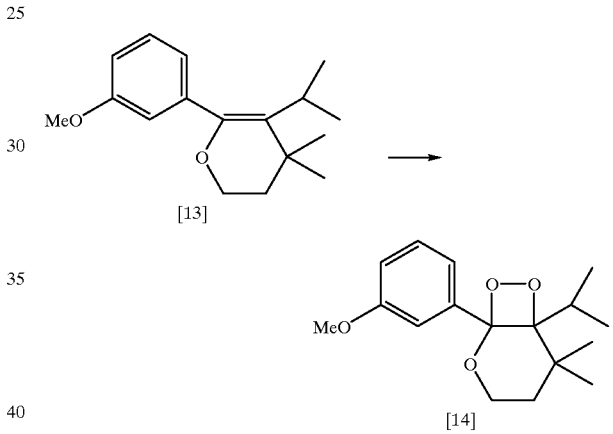

Under an oxygen atmosphere at 0° C., 1.6 mg of TPP and 101.0 mg (0.388 mmol) of 5-isopropyl-6-(3-methoxyphenyl)-4,4-dimethyl-2,3-dihydropyran (compound [13]) were added to 5 mL of bichloroform and the mixture was externally irradiated for one hour and a half using a 940 W sodium lamp. The reaction solution was concentrated, and then the concentrate was eluted by subjecting it to a silica gel column using a mixed solvent of ether and hexane (1:20) as an eluent to obtain 67.9 mg of 6-isopropyl-(3-methoxyphenyl)-5,5-dimethyl-2,7,8-trioxabicyclo[4.2.0]octane (compound [14]) as a yellow oily product (yield: 59.9%).

$^1$HNMR (400 MHz, CDCl$_3$); δ0.72 (d, J=7.2 Hz, 3H), 0.81 (d, J=7.2 Hz, 3H), 1.05 (s, 3H), 1.37 (s, 3H), 1.37 (ddd, J=13.4, 7.8 and 1.7 Hz, 1H), 2.41 (sept, J=7.2 Hz, 1H), 3.05 (ddd, J-13.4, 10.6 and 9.0 Hz, 1H), 3.84 (s, 3H), 4.23 (dt, J=10.6 and 7.8 Hz, 1H), 4.40 (ddd, J=10.6, 9.0 and 1.7Hz, 1H), 6.89–6.94 (m, 1H), 7.29–7.32 (m, 3H) ppm.

$^{13}$CNMR (100 MHz, CDCl$_3$); δ18.2, 18.7, 24.0, 25.1, 33.4, 36.6, 55.4, 61.0, 96.6, 108.9, 113.4, 114.6, 120.2, 128.7, 139.6, 159.2 ppm.

IR (liquid film); 2967, 1718, 1586, 1488, 1458, 1277, 1049 cm$^{-1}$.

Reference Example 9

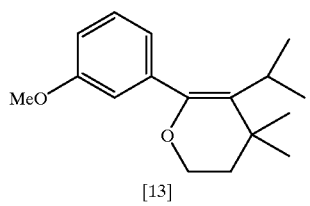

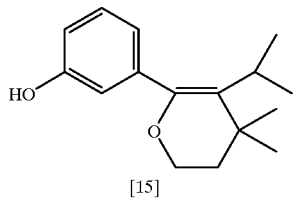

Under a nitrogen atmosphere, 0.24 mg (2.30 mmol) of 60% sodium hydride was added to 2 mL of DMF and 0.21 mL (2.88 mmol) of entathiol was added at 0° C., and then a solution prepared by dissolving 0.30 g (1.15 mmol) of 35-isopropyl-6-(3-methoxyphenyl)-4,4-dimethyl-2,3-dihydropyran (compound [13]) in 2 mL of DMF was added at 0° C. After the completion of a dropwise addition, the mixture was heated at 140° C. for five hours. The reaction solution was extracted with ethyl acetate, washed in turn with an aqueous saturated ammonium chloride solution and a saturated sodium chloride solution, and then concentrated by drying over magnesium sulfate. The concentrate was eluted by subjecting it to a silica gel column using a mixed solvent of ethyl acetate and hexane (1:5) as an eluent to obtain 0.25 g of 6-(3-hydroxyphenyl)5-isopropyl-4,4-dimethyl-2,3-dihydropyran(compound [15]) as a colorless oily product (yield: 87.0%).

Melting point; 140.7–141.0° C. (columnar crystal, recrystallized from a mixed solvent of methylene chloride and hexane).

$^1$HNMR (400 MHz, CDCl$_3$); δ0.90 (d, J=7.3 Hz, 6H), 1.18 (s, 6H), 1.18 (s, 6H), 1.17–1.74 (m, 2H), 2.43 (sept, J=7.2 Hz, 1H), 4.02–4.05 (m, 2H), 4.95 (s, 1H), 6.72–6.75 (m, 2H), 6.85 (d with fine coupling, J=7.32 Hz, 1H), 7.15–7.19 (m, 1H) ppm.

$^{13}$CNMR (100 MHz, CDCl$_3$); δ24.0, 27.4, 28.7, 32.6, 39.9, 62.9, 115.0, 117.4, 122.6, 122.7, 128.9, 139.8, 148.0, 155.0 ppm.

IR (KBe); 3410, 2962, 2922, 2872, 1655, 1597, 1016, 711 cm$^{-1}$.

Reference Example 10

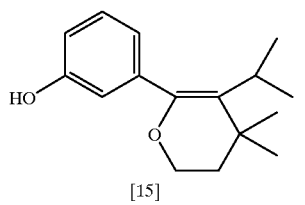

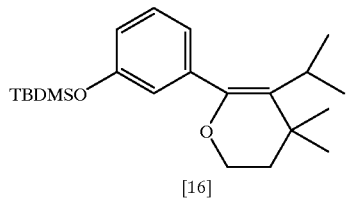

Under a nitrogen atmosphere, 0.23 g (0.94 mmol) of 6-(3-hydroxyphenyl)-5-isopropyl-4,4-dimethyl-2,3-dihydropyran (compound [15]), 0.13 g (1.89 mmol) of imidazole and 0.26 g (1.70 mmol) of t-butyldimethylchlorosilane were added to 2 mL of DMF, followed by stirring at room temperature for 1.5 hours. The reaction solution was extracted with ethyl acetate, washed with a saturated sodium chloride solution, and then concentrated by drying over magnesium sulfate. The concentrate was eluted by subjecting it to a silica gel column using a mixed solvent of hexane and ethyl acetate (1:6) as an eluent to obtain 0.33 g of 6-(3-t-butyldimethylsiloxyphenyl)-5-isopropyl-4,4-dimethyl-2,3-dihydropyran (compound [16]) as a colorless solid (yield: 97.1%).

Melting point; 35.4–35.9° C. (needle crystal).

$^1$HNMR (400 MHz, CDCl$_3$); δ0.18 (s, 6H), 0.89 (d, J=6.8 Hz, 6H), 0.98 (s, 9H), 1.18 (s, 6H), 1.71–1.74 (m, 2H), 2.43 (sept, J=7.2 Hz, 1H), 4.01–4.04 (m, 2H), 6.75–6.78 (m, 2H), 6.87 (d with fine coupling, J=7.5 Hz, 1H), 7.16 (t, J=7.5 Hz, 1H) ppm.

$^{13}$CNMR (100 MHz, CDCl$_3$); δ-4.4, 18.1, 24.1, 25.7, 27.4, 28.8, 32.6, 40.0, 62.8, 119.4, 121.9, 122.0, 123.4, 128.5, 140.0, 148.4, 155.0 ppm.

IR (liquid film); 2957, 2930, 2861, 1480, 1306, 1252, 953 cm$^{-1}$.

Example 4

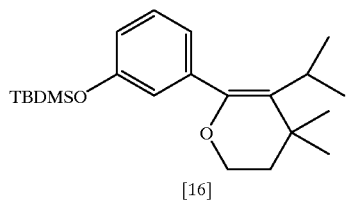

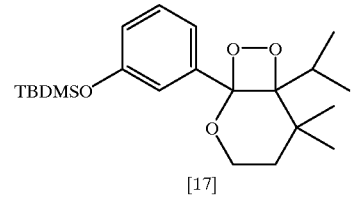

Under an oxygen atmosphere at 0° C., 1.5 mg of TPP and 45.7 mg (0.127 mmol) of 6-(3-t-butyldimethylsiloxyphenyl)-5-isopropyl-4,4-dimethyl-2,3-dihydropyran (compound [16]) were added to 3 mL of bichloroform and the mixture was irradiated with visible light for one hour. The reaction solution was concentrated and then eluted by subjecting it to a silica gel column using a mixed solvent of ether and hexane (1:30) as an eluent to obtain 42.4 mg of 1-(3-t-butyldimethylsiloxyphenyl)-6-isopropyl-5,5-dimethyl-2,7,8-trioxabicyclo[4.2.0]octane (compound [17]) as a yellow oily product (yield: 85.3).

$^1$HNMR (400 MHz, CDCl$_3$); δ0.19 (s, 6H), 0.70 (d, J=7.2 Hz, 3H), 0.82 (d, J=7.2 Hz, 3H), 0.99 (s, 9H), 1.04 (s, 3H), 1.35 (s, 3H), 1.37 (ddd, J=13.2, 7.8 and 1.9 Hz, 1H), 2.44 (sept, J=7.2 Hz, 1H), 3.03 (ddd, J=13.2, 10.7 and 7.8 Hz, 1H), 4.23 (dt, J=10.7 and 7.8 Hz, 1H), 4.41 (ddd, J=10.7, 8.9 and 1.9 Hz, 1H), 6.84 (ddd, J=7.8, 2.4 and 1.5 Hz, 1H), 7.30–7.31 (m, 3H) ppm.

$^{13}$CNMR (100 MHZ, CDCl$_3$); δ-4.4, 18.1, 18.3, 24.0, 25.1, 33.4, 35.2, 36.6, 60.9, 96.5, 108.8, 119.8, 120.7, 120.8, 128.7, 139.6, 155.3 ppm.

IR (liquid film); 2929, 1859, 1721, 1602, 1585, 1485, 1436, 1293, 1211 cm$^{-1}$.

Experiment 1

1 ml of a solution of 6-t-butyl-1-(3-t-butyldimethylsiloxy)phenyl-5,5-dimethyl-2,7,8-trioxabicyclo[4.2.0]octane (compound [8]) obtained in Example 2 in 1.00×10$^{-5}$ M DMSO was added to 2 ml of a solution of tetrabutylammonium fluoride in 1.00×10$^{-2}$ M DMSO at 25° C., and then light emission was determined by using a fluorometric analyzer. It was estimated that the light emission quantum efficiency is 0.40, the half-life of light emission is 13.2 seconds and max is 466 nm.

Experiment 2

10 mg of 6-t-butyl-1-(3-t-butyldimethylsiloxy)phenyl-5,5-dimethyl-2,7,8-trioxabicyclo[4.2.0]octane (compound [8]) obtained in Example 2 was dissolved in toluene-d$_8$ (0.35 mL). The resulting solution was heated in a temperature constant bath at 80, 90 and 100° C. and HNMR was measured with a lapse of time, and then the reaction rate constant at each temperature was calculated. As a result, it was estimated that the half-life of light emission at 25° C. is 49.2 years.

As described above, according to the present invention, the 1,2-dioxetane derivative (I) of the present invention is a compound which can be stored without being refrigerated because of high thermal stability, and a compound capable of emitting light in a stable state with a very high quantum efficiency. Therefore, the measurement of light emission can be efficiently effected because of its freedom from special requirements in storage, easy handling and very high efficiency of light emission. The above derivative is useful for attaining high-sensitivity measurements in, for example, the field of immunoassay of clinical analysis.

What is claimed is:

1. A 1,2-dioxetane derivative represented by the general formula (I):

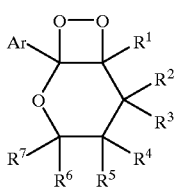

(I)

wherein R$^1$, R$^2$, R$^3$, R$^4$, R$^5$, R$^6$ and R$^7$ independently represents a hydrogen atom, an alkyl group or an aryl group; or one or more than one pair of R$^2$ and R$^3$, R$^4$ and R$^5$, and R$^6$ and R$^7$ can together form a cyclic alkyl group; and Ar represents a group represented by the formula (A):

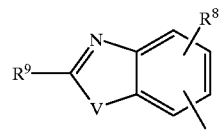

(A)

wherein R$^8$ represents a hydroxyl group, an alkoxyl group, an aralkyloxy group, a group represented by —OSi(R$^{10}$R$^{11}$R$^{12}$) wherein R$^{10}$, R$^{11}$ and R$^{12}$ independently represents an alkyl group, or a phosphate group; R$^9$ represents a hydrogen atom, an alkyl group, an aryl group, a hydroxyl group, an alkoxyl group, an aryloxy group, or an aralkyloxy group; and V represents an oxygen atom or a sulfur atom, a group represented by the formula (B):

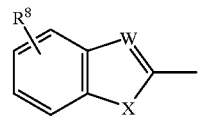

(B)

wherein R$^8$ has the same meaning as defined for R$^8$ in the above formula (A); W represents a nitrogen atom or C—R$^{13}$
wherein R$^{13}$ represents a hydrogen atom, an alkyl group, an aryl group, an alkoxyl group, or an aralkyloxy group; and X represents oxygen atom or sulfur atom, or a group represented by the formula (C):

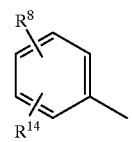

(C)

wherein R$^8$ has the same meaning as defined for R$^8$ in the above formula (A); R$^{14}$ represents a hydrogen atom, a halogen atom, an alkyl group, an alkoxyl group, or a group represented by the formula (R$^{14'}$):

(R$^{14'}$)

wherein Y represents an oxygen atom, a sulfur atom, or a group represented by N—R$^{15}$; and Z represents a hydrogen atom, an alkyl group, an aryl group, or a group represented by —OR$^{16}$, —SR$^{17}$ or the formula:

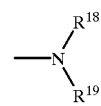

wherein R$^{15}$ represents a hydrogen atom, an alkyl group, an aryl group, a hydroxyl group, or an alkoxyl group; and R$^{16}$, R$^{17}$, R$^{18}$ and R$^{19}$ represent a hydrogen atom, an alkyl group, or an aryl group, or one or more than one pair of R$^{15}$ and $R^{16}$, $R^{15}$ and $R^{17}$, $R^{15}$ and $R^{18}$, and $R^{18}$ and $R^{19}$ can together form a ring and this ring may contain two or more heteroatoms.

2. The 1,2-dioxetane derivative according to claim 1, wherein Ar is a group represented by the formula (a):

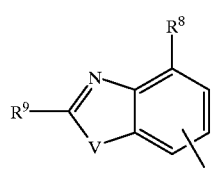

(a)

wherein $R^8$, $R^9$ and V have the same meaning as defined for $R^8$, $R^9$ and V in the above formula (A), a group represented by the formula (b):

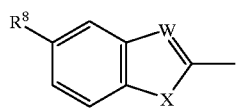

(b)

wherein $R^8$, W and X have the same meaning as defined for $R^8$, W and X in the above formula (B), or a group represented by the formula (c):

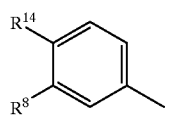

(c)

wherein $R^8$ and $R^{14}$ are the same as those in the above formula (C).

3. The 1,2-dioxetane derivative according to claim 1, wherein $R^1$, $R^2$ and $R^3$ are alkyl groups; and $R^4$, $R^5$, $R^6$ and $R^7$ are hydrogen atoms.

4. The 1,2-dioxetane derivative according to claim 3, wherein $R^1$, $R^2$ and $R^3$ are alkyl groups having 1 to 4 carbon atoms.

5. The 1,2-dioxetane derivative according to claim 1, wherein Y is an oxygen atom and Z is a group represented by the formula:

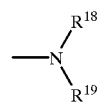

wherein $R^{18}$ and $R^{19}$ together form a 3- to 7-membered ring.

6. The 1,2-dioxetane derivative according to claim 5, wherein $R^{18}$ and $R^{19}$ together form a group represented by the formula:

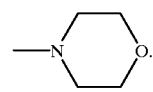

7. The 1,2-dioxetane derivative according to claim 1, wherein Y is N—$R^{15}$, Z is —$OR^{16}$, and $R^{15}$ and $R^{16}$ together form a 3- to 7-membered ring.

8. The 1,2-dioxetane derivative according to claim 7, wherein $R^{15}$ and $R^{16}$ together form a group represented by the formula:

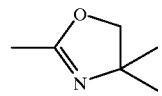

9. A reagent for immunoassay, comprising the 1,2-dioxetane derivative of claim 1.

10. An immunoassay method, which comprises using the reagent for immunoassay of claim 9.

* * * * *